United States Patent [19]

Hamill et al.

[11] Patent Number: 4,830,967

[45] Date of Patent: May 16, 1989

[54] PROCESS FOR PRODUCING ANTIBIOTIC A80438

[75] Inventors: Robert L. Hamill, Greenwood; Raymond C. Yao, Carmel, both of Ind.

[73] Assignee: Eli Lilly and Company, Indianapolis, Ind.

[21] Appl. No.: 738,317

[22] Filed: May 28, 1985

[51] Int. Cl.$^4$ .................. C12R 1/465; C12P 17/16; C12P 17/02

[52] U.S. Cl. .................. 435/253.5; 435/118; 435/123; 435/886; 435/126

[58] Field of Search .............. 536/16.8, 18.1; 514/25; 435/886, 253, 126, 119, 118, 123; 549/343

[56] References Cited

U.S. PATENT DOCUMENTS

| | | | |
|---|---|---|---|
| 3,183,154 | 5/1965 | Argoudelis et al. | 167/65 |
| 3,950,514 | 4/1976 | Sawada | 424/121 |
| 4,591,559 | 5/1986 | Liu et al. | 435/76 |

FOREIGN PATENT DOCUMENTS

A-2322596 4/1977 France.

OTHER PUBLICATIONS

T. Mizutani et al., "Lonomycins B and C: Two New Components of Polyether Antibiotics: Fermentation Isolation and Characterization," *J. Antibiotics* 33, 1224–1230 (1980).

J. W. Westley: "Polyether Antibiotics," vol. 1, pp. 1–11, 12 Chapter 1, Marcel Dekker Inc., New York.

Taylor et al., ibid., pp. 103 and 109–110.

S. Omura et al., "Isolation of a New Polyether Antibiotic, Lonomycin," *J. Antibiotics* 29 (1), 15–20 (1976).

C. Riche et al., "Crystal and Molecular Structure of Emericid: A New Polyether Antibiotic," J. C. S. Chem. Comm. 1975, 951–952.

M. Ohshima et al., "Antibiotic DE-3936, a Polyether Antibiotic Identical with Lonomycin; Taxonomy, Fermentation, Isolation and Characterization," *J. Antibiotics* 29 (4), 354–365 (1976).

N. Tsuji et al., "Two New Antibiotics, A-218 and K-41; Isolation and Characterization," *J. Antibiotics* 29 (1) 10–14 (1976).

*Primary Examiner*—Charles F. Warren
*Assistant Examiner*—Irene Marx
*Attorney, Agent, or Firm*—Nancy J. Harrison; Leroy Whitaker

[57] ABSTRACT

A new strain of *Streptomyces pactum*, NRRL 15970, and an improved fermentation process for producing the polyether antibiotic A80438 using this microorganism are provided.

4 Claims, No Drawings

PROCESS FOR PRODUCING ANTIBIOTIC A80438

SUMMARY OF THE INVENTION

This invention relates to a new microorganism, *Streptomyces pactum* NRRL 15970, which produces the polyether antibiotic A80438. This invention also relates to a process for producing A80438 by culturing the novel strain of *Streptomyces pactum* NRRL 15970 under submerged aerobic fermentation conditions until a substantial level of the antibiotic is produced. A80438 is extracted from the fermentation broth and from the mycelium with polar organic solvents and is separated and further purified by techniques such as column chromatography.

A80438 is an antibacterial and anticoccidial agent. It also improves feed-utilization efficiency in ruminants and acts as a growth promotant in monogastric animals.

DETAILED DESCRIPTION OF THE INVENTION

Improved methods for producing antibiotics are of great importance. Commonly, cultures isolated from the natural state (the "wild types") produce the antibiotic in low yield. Often, antibiotic production is erratic. Strains which produce antibiotics in greater yield and strains which produce them consistently are, therefore, of great value.

This invention provides an improved process for preparing antibiotic A80438 by culturing an A80438-producing strain of *Streptomyces pactum* NRRL 15970 under submerged aerobic conditions in a suitable culture medium until substantial antibiotic activity is produced. The antibiotic is recovered using various isolation and purification procedures understood in the art.

Antibiotic A80438 is a new member of the group of polyether antibiotics. Westley (John W. Westley, "Polyether Antibiotics: Naturally Occurring Acid Ionophores, Vol 2, Chemistry," Marcel Dekker: New York, 1983) has separated existing polyethers by class and type. Using Westley's system, A80438 is a new member of the Class 1a, type (2), group of polyethers. Examples of other members of this group are: Ionomycin (also called emericid, A218, RP 31559 and DE 3936; see U.S. Pat. No. 3,950,514), monensin (U.S. Pat. No. 3,501,568), nigericin and laidlomycin.

Antibiotic A80438 and a method for producing the antibiotic using a strain of *Streptomyces bobili* (NRRL 19571) are described by Robert L. Hamill, Walter M. Nakatsukasa and Raymond C. Yao in their co-pending application entitled "ANTIBIOTIC A80438 AND PROCESS FOR ITS PRODUCTION", attorney docket No. X-6663, Ser. No. 06/738,320 May 28,1985.

Characteristics of A80438

Antibiotic A80438 has been assigned structure 1, based on its physico-chemical characteristics:

A80438 (in its sodium salt form) has the following characteristics:
State: white crystals (from acetone-water)
mp: 160°–162° C.
pKa:=5.2 (66% aqueous dimethylformamide)
$[\alpha]^{25}D: +102°$ (c 1, CHCl$_3$)
Molecular weight: 820 by field desorption mass spectrometry (FDMS)
Empirical formula: $C_{43}H_{74}O_{13}Na$
UV: no absorbance
IR (acid form, CHCl$_3$) 3018, 2976, 2940, 1731, 1457, 1379, 1206, 1118, 1088, 1041, 1021, 978, and 968 cm$^{-1}$.
IR (Na salt, CHCl$_3$) 3018, 2979, 2938, 2881, 2832, 1710, 1591, 1454, 1387, 1306, 1243, 1215, 1170, 1117, 1089, 1076, 974, 967 and 874 cm$^{-1}$.
Solubility: Not very soluble in water; soluble in dimethyl sulfoxide, dimethylformamide, lower alcohols such as methanol, ketones such as acetone, esters such as ethyl acetate, halogenated hydrocarbons such as chloroform and hydrocarbons such as diethyl ether, benezene, toluene and warm hexane.

As is apparent from its structure, A80438 has an acid function capable of forming salts and ester derivatives. A80438 also has at least one hydroxyl group which can be esterified or which can form ether derivatives. A80438, its acyl and alkyl ester and alkyl ether derivatives, and the pharmaceutically-acceptable salts of A80438 and of these derivatives are useful as antibiotics and as agents which increase feed-utilization efficiency.

The microorganism of this invention, which has been designated *Streptomyces pactum*, is useful for the preparation of antibiotic A80438. This microorganism was isolated from a soil sample from New Jersey. A culture of the *Streptomyces pactum* strain of this invention has been deposited and made part of the stock culture collection of the Midwest Area Northern Regional Research Center, Agricultural Research Service, U.S. Department of Agriculture, 1815 North University Street, Peoria, Ill. 61604, from which it is available to the public under the accession number NRRL 15970.

Taxonomic studies of this organism were carried out by Frederick P. Mertz of the Lilly Research Laboratories. Based on these studies, the organism is classified as a new strain of *Streptomyces pactum* Bhuyan, Dietz and Smith 1962. This classification is based on an examination of published descriptions of this species [R. E. Buchanan, and N. E. Gibbons (eds), "Bergey's Manual of Determinative Bacteriology", 8th Edition, The Williams and Wilkins Co., Baltimore, 1974; and E. B. Shirling, and D. Gottlieb, "Cooperative Description of Type Cultures of Streptomyces", *Int. J. Syst. Bacteriol.* 22(4):265–394 (1972)].

For convenience the new *Streptomyces pactum* strain is called the A80373 culture in the following discussion of its characteristics.

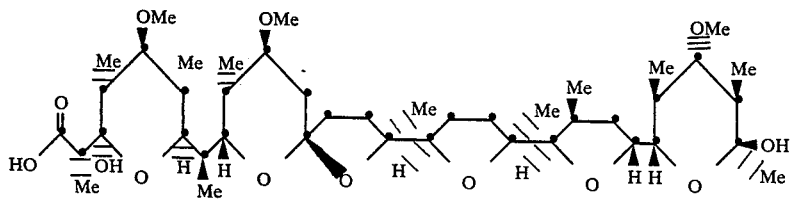

1

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)]have been followed.

Carbon utilization was determined on ISP No. 9 basal medium to which filter-sterilized carbon sources were added to equal a final concentration of 1.0 percent. Plates were incubated at 30° C. and read after 14 days.

Melnnoid pigment production (chromogenicity) was determined with ISP No. 1 (tryptone-yeast extract broth), ISP No. 6 (peptone-yeast extract iron agar) and ISP No. 7 (tyrosine agar).

Starch hydrolysis was determined by testing for the presence of starch with iodine on ISP No. 4 (inorganic salts-starch agar) plates (D. J. Blazevic and G. M. Ederer, "Principles of Biochemical Tests in Diagnostic Microbiology", John Wiley and Sons, Inc., New York, 1975, p. 136).

Morphology was studied using an optical light microscope. A scanning electron microscope (SEM) was used to study the spore surface ornamentation.

NaCl tolerance was measured by adding NaCl to ISP No. 2 agar to equal the concentration desired.

ICSS-NBS Centroid Color Charts, standard sample No. 2106 (National Bureau of Standards, U.S. Department of Commerce, Washington, D.C., 1958) and the Color Harmony Manual (4th ed,, Color Standards Department, Container Corporation of America, Chicago, Ill., 1958) were used to assign color names.

The isomer of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates", *Appl. Microbiol.* 12, 421–423 (1964)]and of Lechevalier [M. P. Lechevalier, "Identification of Aerobic Actinomycetes of Clinical Importance", *J. Lab. Clin. Med.* 71, 934–944 (1968)].

Resistance to antibiotics was measured by padding antibiotic sensitivity discs onto the surface of seeded ISP No. 2 agar plates.

Cultural Characteristics

A total of 15 agar media were used to study the cultural characteristics of this strain. Although abundant growth was observed on a number of the media, good aerial production was limited to only a few media. The culture formed aerial hyphae in the gray color series on yeast malt extract agar (ISP No. 2), glycerol asparagine agar (ISP No. 5), glucose-asparagine agar, tomato pasteoatmeal agar and tyrosine agar (ISP No. 7). The nearest matching color tab is (d) light Gray in the Tresner and Backus system [H D. Tresner and E. J. Backus, "System of Color Wheels for Streptomycete Taxonomy," *Appl. Microbiol.* 11:335–338 (1956)]. Very poor growth and aerial production were observed on oatmeal agar (ISP No. 3), Czapek's agar, Anio-Hensens agar and potato-carrot agar. Sporemass color on these media was white. Growth was not observed on starch salts (ISP No. 4) or tap water agar. Coremia and sterile aerial hyphae were produced on a number of agar media. A80373 is placed in the gray color series.

The reverse side of A80373 is yellow-brown to dark reddish-brown, depending on the medium. A light brown soluble pigment is present when the culture is grown in ISP Nos. 2, 5 and 7 media. The cultural characteristics on six key media are presented in Table 1.

TABLE 1

Cultural Characteristics of A80373 on Selected Agar Media

| Medium | Characteristics |
|---|---|
| Yeast Malt. Ext. (ISP No. 2) | G: Good<br>R: 75. deep y Brown<br>Am: Fair: (g) medium Gray<br>Sp: Light brown |
| Glycerol Asparagine (ISP No. 5) | G: Abundant<br>R: 47. d. gy. reddish Brown<br>Am: Abundant: (5fe) l. gy. r. Brown<br>Sp: Light brown |
| Czapek's Solution Agar | G: Trace (excellent sporophores)<br>R: 263. White<br>Am: Trace: (a) White(scattered clumps)<br>Sp: None |
| Tomato Paste Oatmeal | G: Fair<br>R: 94. l. olive Brown<br>Am: Fair: (d) light Gray<br>Sp: None |
| Glucose-Asparagine Agar | G: Good (coremia)<br>R: 75. deep y Brown<br>Am: Fair: (2 ge) l. olive Brown<br>Sp: None |
| Tyrosine Agar (ISP No. 7) | G: Abundant<br>R: 47. d. gy. reddish Brown<br>Am: Abundant: (2dc) y Gray<br>Sp: Brown |

G = Growth
R = Reverse
Am = Aerial Mycelia
Sp = Soluble Pigment

Morphological Characteristics

A80373 produces sterile aerial hyphae on ISP No. 5 and 7 media and on glucose-asparagine agar. The culture produces coremia on Emerson, glucose-asparagine and yeast dextrose agars.

Coiled sporophores of 3–5 turns are seen on a number of media. This is best illustrated on Czapek's solution agar. Culture A80373 is placed in the Spirales (S) section of Pridham [T. G. Pridham and A. J. Lyons, Jr., "Progeess in Clarification of the Taxonomic and Nomenclatural Status of Some Problem Actinomycetes", In "Developments In Industrial Microbiology", Vol. 10, American Institute of Biological Sciences, Washington, D.C., 1969]. Spores are arranged in chains of 10 to 50.

When examined by scanning electron microscopy, the spore-surface ornamentation is either spiny (sp) or hairy (ha) with very short non-characteristics hairs.

Physiological Characteristics

Analysis of hydrolyzed whole cells indicates that LL-DAP is present, but the meso isomer is not present. Thus, A80373 has a type I cell wall (Lechevalier, supra). Sugar components of whole cells are glucose, arabinose and rhamnose. Although arabinose is normally absent from cell walls of Streptomyces, Pridham, supra, lists species where it is present. The sugar pattern is classified as NC (not characteristic). Culture A80373 is classified as belonging to the genus Streptomyces.

The carbon-utilization pattern for A80373 is as follows: A80373 uses adonitol, fructose, glucose and ribose. A80373 does not use L-arabinose, cellobiose, cellulose, dextran, galactose, inositol, inulin, lactose, mannitol, mannose, melezitose, melibiose, raffinose, L-rhamnose, salicin, sucrose, trehalose, xylitol or xylose.

Culture A80373 is resistant to cephalothin (30 μg), lincomycin (2 μg), penicillin G (10 units) and streptomycin (10 μg). It is sensitive to bacitracin (10 units), gentamicin (10 μg), neomycin (30 μg), oleandomycin (15 μg), rifampin (5 μg), tetracycline (30 μg), tobramycin (10 μg) and vancomycin (30 μg).

Culture A80373 does not reduce nitrate to nitrite in organic nitrate broth (ISP No. 8) or hydrolyze skim milk or starch. It does produce catalase, liquefy gelatin, hydrolyze calcium malate, and survive at 50° C. for 8 hours. A80373 will tolerate only 1% NaCl, and will grow at temperatures between 5 and 30° C. Melanoid pigments are not produced when A80373 is grown in tryptone yeast extract broth (ISP No. 1) or on slants of peptone yeast extract iron agar (ISP No. 6) and ISP No. 7.

A comparison of A80373 and another A80438-producing strain, Streptomyces bobili NRRL 15971, indicates that, although they share many common characteristics, and both produce the same antibiotic, they are separate species. The following list summarizes this data.

| Comparison of Culture A80373 and Streptomyces bobili NRRL 15971 | |
|---|---|
| Similarities | Differences |
| Absence of melanoid pigments | Antibiotic-resistance pattern |
| Calcium malate hydrolysis | Carbon-utilization pattern |
| Catalase production | Cultural characteristics: |
| Coremia formation | Aerial hyphae |
| Skim milk reaction, negative | Reverse color |
| Starch hydrolysis, negative | Soluble pigment |
| Sugar components in cell wall | Gelatin liquefaction |
| | Morphology |
| | NaCl tolerance |
| | Nitrate reduction |
| | Spore surface ornamentation |
| | Survival at 50° C., 8 h. |
| | Temperature range |

Species Determination

Using several "keys" to the species of Streptomyces, the cultural, morphological and physiological characteristics of A80373 were used to select a group of strains with similar characteristics. The published descriptions were then examined, and compared with A80373. The following six species were selected as having close resemblance to A80373:

Streptomyces albulus[a]
Streptomyces chattanoogensis[b]
Streptomyces craterifer[c]
Streptomyces galteri[a]
Streptomyces karnatakensis[c]
Streptomyces pactum[a] 6 [a]E. B. Shirling and D. Gottlieb, "Cooperative Description of Type Cultures of Streptomyces," Int. J. Syst. Bacteriol. 22(4): 265-394 (1972) 6 [b]E. B. Shirling and D. Gottlieb, "Cooperative Description of Type Cultures of Streptomyces," Int. J. Syst. Bacteriol. 18(2): 69-189 (1968) 6 [c]E. B. Shirling and D. Gottlieb, "Cooperative Description of Type Cultures of Streptomyces," Int. J. Syst. Bacteriol. 19(4): 375-512 (1969)

A close inspection of the published data shows that A80373 has the most characteristics in agreement with S. karnatakensis. In addition, A80373 keyed directly to this species in several instances.

S. karnatakensis and S. pactum are clustered closely together in two independent numerical phenetic studies [W. Kurylowicz, A. Paszkiewicz, W. Woznicka, and W. Kurzatkowski, "Numerical Taxonomy of Streptomycetes," Polish Medical Publishers, Warsaw, 1975; and S. T. Williams, M. Goodfellow, G. Alderson, E. M. H. Wellington, P. H. A. Sneath and M. J. Sackin, "Numerical Classification of Streptomyces and Related Genera," J. Gen. Microbiol. 129, 1743-1813 (1983)]. Williams states that they are joined together at a 96% similarity level. He drops the name S. karnatakensis and uses S. pactum as the cluster name. Of the two names, only S. pactum is in the Approved Lists [V. B. D. Skerman, et al, "Approved Lists of Bacterial Names," Int. .J. Syst. Bacteriol. 30(1): 225-420 (1980)]; consequently, it is the only one validly published. The name S. pactum, therefore, will be used.

Culture A80373 and S. pactum both belong to the gray color series, exhibit similar reverse side color, have some soluble pigments, grow poorly on Czapek's agar, have almost identical carbon-utilization patterns, possess spiral morphology and hairy spores. Neither produces melanoid pigments. They differ in their growth on glycerol asparagine and oatmeal agars, ability to produce coremia, hydrolysis of calcium malate and NaCl tolerance.

The similarities and differences between A80373 and S. pactum are summarized below:

| Similarities | Differences |
|---|---|
| Absence of melanoid pigments | Calcium malate hydrolysis |
| Aerial spore mass color | Coremia |
| Carbon-utilization pattern | Growth on several media |
| Cultural features on Czapek's agar | NaCl tolerance |
| Reverse side color | |
| Soluble pigments | |
| Spiral sporophore morphology | |
| Spore-surface ornamentation | |

The carbon-utilization patterns of these two cultures are shown in Table 2.

TABLE 2

| Utilization of Carbon Sources by Strain A80373 and S. pactum NRRL 2939 | | |
|---|---|---|
| Carbon Source | A80373 | S. pactum |
| None | − | − |
| L-Arabinose | − | − |
| D-Fructose | + | + |
| D-Galactose | − | + |
| D-Glucose | + | + |
| i-Inositol | − | − |
| D-Mannitol | − | − |
| Raffinose | − | − |
| L-Rhamnose | − | − |
| Salicin | − | − |
| Sucrose | − | − |
| D-Xylose | − | − |

+ = Utilized
− = Not Utilized

A lssting of characteristics of A80373 is shown in Table 3.

TABLE 3

| Physiological Characteristics of A80373 | |
|---|---|
| Characteristic | A80373[a] |
| Catalase production | + |
| Gelatin liquefaction | + |
| Hydrolysis calcium malate | + |
| Hydrolysis skim milk | − |
| Hydrolysis starch | − |
| Melanoid pigmentation | − |

TABLE 3-continued

Physiological Characteristics of A80373

| Characteristic | A80373[a] |
|---|---|
| NaCl tolerance | 1% |
| Nitrate reduction | − |
| Resistance to cephalothin | + |
| Resistance to lincomycin | + |
| Resistance to penicillin G | + |
| Resistance to streptomycin | + |
| Survival at 50° C., 8 h | + |
| Temperature range for growth | 5–30° C. |
| Utilization of: | |
| adonitol | + |
| cellobiose | − |
| cellulose | − |
| dextran | − |
| inulin | − |
| lactose | − |
| mannose | − |
| melezitose | − |
| melibiose | − |
| ribose | + |
| trehalose | − |
| xylitol | − |

[a] + = positive reaction
− = negative reaction

These comparisons demonstrate that A80373 is similar to *S. pactum*. Although the spore surface of A80373 is not unmistakably hairy as is *S. pactum*, the differences are not considered sufficient to assign A80373 to a different species. Therefore, culture A80373 is classified as a strain of *Streptomyces pactum* Bhuyan, Dietz and Smith 1962.

As is the case with other organisms, the characteristics of the A80438-producing culture of this invention, *Streptomyces pactum* NRRL 15970, are subject to variation. Mutants of the strain may be obtained by methods in the art. For example, mutants can be obtained by treatment with various known physical and chemical mutagens such as ultraviolet light, X rays, gamma rays and chemicals such ss N-methyl-N'-nitro-N-nitrosoguanidine. Natural and induced variants, mutants and recombinants of *Streptomyces pactum* NRRL 15970 which retain the characteristic of A80438 production are part of this invention.

The culture medium used to grow *Streptomyces pactum* NRRL 15970 can be any one of a number of media. For economy in production, optimal yield, and ease of product isolation, however, certain culture media are preferred. Thus, for example, a preferred carbohydrate source in large-scale fermentation is glucose, although sucrose, fructose, blackstrap molasses, starch and the like can also be used.

A preferred nitrogen source is enzyme-hydrolyzed casein although meat peptones, fish meal, liver meal, an the like are also useful.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 ml/L) of an antifoam agent such as polypropylene glycol may be added to large scale fermentation media if needed.

For production of substantial quantities of antibiotic A80438, submerged aerobic fermentation in tanks is preferred. Small quantities of A80438 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80438 is produced by *Streptomyces pactum* NRRL 15970 when grown at temperatures between about 25° and about 37° C. An optimum temperature for A80438 production appears to be about 30° C.

As is customary in submerged aerobic culture processes, sterile air is blown into the vessel from the bottom while the medium is stirred with conventional turbine impellors. Under the conditions used thus far, the maximum oxygen uptake of the fermentation does not exceed about 0.2 mM/L/minute. For example, in a fully baffled 165-liter fermentor containing approximately 115 liters of broth, an aeration rate of 0.125 v/v/m with an agitation rate of 150-200 rpm is sufficient to maintain the level of dissolved oxygen at or above 30% of air saturation.

Production of antibiotic A80438 can be followed during the fermentation by testing samples of the broth for antibiotic activity against organisms known to be sensitive to the antibiotic. One assay organism useful in testing A80438 is *Bacillus subtilis* ATCC 6633. The bioassay is conveniently performed by the agar-well plate test.

Following its production under submerged aerobic fermentation conditions, A80438 can be recovered from the fermentation medium by methods used in the fermentation art. The antibiotic activity produced during fermentation of the A80438-producing organism occurs both in the filtered broth and in the mycelial mass. Maximum recovery of A80438 is accomplished, therefore, by initially filtering the medium to separate the broth from the mycelial mass. The filtered broth and the mycelial mass can then be purified separately to give their respective portion of A80438. A variety of techniques may be used in this purification.

A preferred technique for purification of the filtered broth involves adjusting it to a pH of about 9 and extracting with a suitable solvent such as, for example, ethyl acetate. The extracting solvent can then be evaporated under vacuum to give the broth portion of A80438.

A preferred method of purifying the mycelial mass is to extract the separated mycelial filter cake with a suitable solvent such as, for example, methanol. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A80438.

The broth and mycelial portions of the A80438 complex are further purified by similar procedures. A preferred procedure involves silica-gel chromatography.

Separation of antibiotic A80438 can be followed by thin-layer chromatography (TLC) or high performance liquid chromatography (HPLC). One convenient silica gel TLC solvent system is toluene:ethanol (4:1). The antibiotic can be detected by bioautography using, for example, *Bacillus subtilis* or by other methods such as, for example, vanillin-sulfuric acid spray reagent.

Alternatively, the culture solids, nncluding medium constituents and mycelium can be used without extraction or separation, but preferably after removal of water, as a source of A80438. For example, after production of A80438, the whole fermentation broth can be dried by lyophilization, by drum-drying, or by azeotropic distillation and drying. The dried broth is then mixed directly into feed premix.

The salts of A80438 and of its derivatives are useful for separating and purifying the antibiotics. The pharmaceutically-acceptable salts are particularly useful. Examples of salts are the alkali-metal, alkaline-earth-metal and amine salts of A80438 and of its derivatives.

The following examples illustrate the operation of this invention.

EXAMPLE 1

Preparation of Antibiotic A80438 Using *Streptomyces pactum* NRRL 15970 (A80373)

A. Shake-flask Fermentation of A80373

The culture *Streptomyces pactum* NRRL 15970, either as a lyophilized pellet or as a suspension maintained in liquid nitrogen, is used to inoculate an agar slant having the following composition:

| Agar-Slant Medium | |
|---|---|
| Ingredient | Amount (g/L) |
| Glucose | 2.5 |
| Soluble Starch | 5.0 |
| Yeast Extract | 1.25 |
| Enzyme-hydrolyzed Casein* | 1.25 |
| $CaCO_3$ | 0.25 |
| Agar | 15.0 |
| Deionized Water | q.s. to 1 liter |

Unadjusted pH = 6.3; adjust to pH 7.5 with NaOH; pH after sterilization = 6.9
*N—Z Amine A, Humko-Sheffield Chemical, Lyndhurst NJ The inoculated slant is incubated at 30? C. for from about 10 to about 14 days. The mature slant culture is scraped with a sterile tool to loosen the spores and remove and macerate the mycelial mat. About one-fourth of the loosened spores and culture growth thus obtained is used to inoculate 50 mL of a first-stage vegetative medium having the following composition:

| Vegetative Medium | |
|---|---|
| Ingredient | Amount (g/L) |
| Glucose | 10 |
| Soluble Starch | 20 |
| Enzyme-hydrolyzed Casein* | 5 |
| Yeast Extract | 5 |
| $CaCO_3$ | 1 |
| Tap water | q.s. 1 liter |

Unadjusted pH = 6.6; adjust to pH 7.2 with NaOH; pH after sterilization = 6.8
*N—Z Amine A The inoculated first-stage medium is incubated in a 250-mL Erlenmeyer flask at 30? C. for about 48 hours on a shaker orbiting in a two-inch (5.08 cm) circle at 250 rpm.

This incubated first-stage medium (1.25 mL) is used to inoculate 50 mL of a production medium having the following composition:

| Ingredient | Amount |
|---|---|
| Glucose | 20 g/L |
| Blackstrap Molasses | 20 g/L |
| Peptone* | 5 g/L |
| $CaCO_3$ | 2 g/L |
| Czapek's Mineral Stock** | 2 mL |
| Deionized water | q.s. 1 liter |

*Bacto Peptone (Difco Laboratories, Detroit MI)
**Czapek's Mineral Stock has the following composition:

| | | |
|---|---|---|
| KCl | 10% | |
| $MgSO_4.7H_2O$ | 10% | |
| $FeSO_4.7H_2O$ | 0.2% | (dissolved in 2 mL of conc. HCl) |
| Deionized water | q.s. to 1 liter | |

The inoculated production medium is incubated in a 250-mL wide-mouth Erlenmeyer flask at 30? C. for 8 to 10 days on a shaker orbiting in a two-inch circle at 250 rpm.

B. Tank Fermentation of A80373

In order to provide a large volume of inoculum, 10 mL of incubated first-stage medium, prepared as described in Section A, is used to inoculate 400 mL of a second-stage growth medium having the same composition as that of the first-stage medium. This second-stage vegetative medium is incubated in a two-liter wide-mouth Erlenmeyer flask for about 48 hours at 30? C. on a shaker orbiting in a two-inch circle at 250 rpm.

Incubated second-stage vegetative medium (400 mL) thus prepared is used to inoculate 100 liters of sterile production medium, prepared as described in Section A. The inoculated production medium is allowed to ferment in a 165-liter stirred fermentation tank for 6 to 8 days at a temperature of 30° C. Low airflow (0.125 v/v/m) and low rpm (150–175) in the stirred vessel maintain a dissolved oxygen level above 30% of air saturation.

EXAMPLE 2

Isolation of A80438 Produced by *Streptomyces pactum*

Whole fermentation broth (114 L), prepared as described in Example 1 and mixed with Hyflo Supercel (3%), was adjusted to pH 3.0 with HCl and filtered through a filter press. The mycelial cake was extracted twice in the press with a solution (30 L) of methanol:-water (9:1) containing 1% $NaHCO_3$. The methanol extracts were combined (60 L), concentrated under vacuum to a volume of 14 L, and adjusted to pH 8.5 with NaOH. The concentrate was extracted twice with ethyl acetate (½ volumes), and the combined extracts (12 L) were concentrated under vacuum to a volume of 0.6 L.

Concentrates obtained in this manner from three 100-L fermentations were combined and evaporated to dryness under vacuum. The residue, dissolved in $CHCl_3$ (200 ml), was applied to a 6×40-cm column of silica gel (1 L, Woelm 100–200 μm) packed in $CHCl_3$. The column was eluted with $CHCl_3$ (6 L) and $CHCl_3$:EtOAc 49:1 (1 L) and 9:1 (4 L)]. Elution was mnnitored by TLC and bioassay. Fractions containing A80438were combined and concentrated under vacuum to dryness.

The residue thus obtained, dissolved in acetone (150 mL), was applied to small amount of silica gel (Woelm 100–200 μm) and dried. The silica gel containing A80438 was then applied to a 6-×40-cm column containing silica gel (1 L, Woelm 100-200 μm) packed in CHCl₃. The column was developed sequentially with CHCl₃ (6 L) and CHCl₃:EtOAc [9:1 (5 L) and 4:1 (2 L)]. Elution was monitored by TLC and bioassay. Fractions containing A80438 were combined and concentrated under vacuum to dryness. The residue obtained was crystallized from acetone to give 14.27 g of crystalline A80438 as the sodium salt.

I claim:

1. A biologically pure culture of the microorganism *Streptomyces pactum* NRRL 15970 or an A80438-producing mutant thereof.

2. The culture of claim 1 which is NRRL 15970.

3. A process for producing antibiotic A80438 which comprises cultivating *Streptomyces pactum* NRRL 15970, or an A80438-producing mutant thereof, in a culture medium containing assimilable sources of carbon, nitrogen and inorganic salts under submerged aerobic ferementation conditions until a recoverable amount of antibiotic A80438 is produced and separating antibiotic A80438 from the culture medium.

4. The process of claim 3 wherein NRRL 15970 is used.

* * * * *